US010506931B1

(12) United States Patent
Baruch

(10) Patent No.: US 10,506,931 B1
(45) Date of Patent: Dec. 17, 2019

(54) NON INVASIVE MONITORING OF ARTERIAL STIFFNESS

(71) Applicant: Empirical Technologies Corporation, Charlottesville, VA (US)

(72) Inventor: Martin Baruch, Charlottesville, VA (US)

(73) Assignee: Empirical Technologies Corporation, Charlottesville, VA (US)

( * ) Notice: Subject to any disclaimer, the term of this patent is extended or adjusted under 35 U.S.C. 154(b) by 561 days.

(21) Appl. No.: 14/636,026

(22) Filed: Mar. 2, 2015

Related U.S. Application Data

(60) Provisional application No. 61/946,277, filed on Feb. 28, 2014.

(51) Int. Cl.
A61B 5/00 (2006.01)
A61B 5/02 (2006.01)
(Continued)

(52) U.S. Cl.
CPC ...... A61B 5/02007 (2013.01); A61B 5/02108 (2013.01); A61B 5/02241 (2013.01); A61B 5/7278 (2013.01)

(58) Field of Classification Search
CPC ... A61B 5/02007; A61B 5/02108; A61B 5/02; A61B 5/0208; A61B 5/021; A61B 5/026; A61B 5/0285
See application file for complete search history.

(56) References Cited

U.S. PATENT DOCUMENTS 6,361,501 B1 * 3/2002 Amano ............ A61B 5/02028
600/485
7,087,025 B2 8/2006 Baruch
(Continued)

OTHER PUBLICATIONS

Ageenkova, Olga, Purygina, Marina, Central aortic blood pressure, augmentation index, and reflected wave transit time: reproducibility and repeatability of data obtained by oscillometry, 2011, Dove Medical Press, pp. 649-656.*
(Continued)

Primary Examiner — Christian Jang
Assistant Examiner — Sarah R Kingsley
(74) Attorney, Agent, or Firm — Kimberly O Snead, Esq.

(57) ABSTRACT

A computer-implemented method for quantifying arterial stiffness and assigning an AS factor uses executable program on a computing device. The arterial pulse of an individual is monitored and the data received from the monitoring member transmitted to the computing device. The data received is processed by the processor, performing a pulse wave analysis. The primary systolic pulse and iliac reflection pulse are extracted from the pulse wave analysis and the time delay between the primary systolic pulse and the iliac reflection pulse determined. The time delay is used to calculate a second derivative based least in part, on the time delay. The frequency above zero components are separated from the second derivative and the area of the second derivative determined between a first primary systolic pulse and a first iliac reflection pulse. A percentage score is calculated based on the degree of arterial stiffness and input into a historical population database comparing the percentage score with the population data.

16 Claims, 11 Drawing Sheets

(51) Int. Cl.
*A61B 5/021* (2006.01)
*A61B 5/022* (2006.01)

(56) References Cited

U.S. PATENT DOCUMENTS

| | | | |
|---|---|---|---|
| 8,100,835 B2 | 1/2012 | Baruch | |
| 2003/0004421 A1* | 1/2003 | Ting | A61B 5/021 600/485 |
| 2003/0199771 A1* | 10/2003 | Baruch | A61B 5/02416 600/485 |
| 2005/0209516 A1* | 9/2005 | Fraden | A61B 5/02055 600/323 |
| 2015/0018632 A1* | 1/2015 | Khair | A61B 5/026 600/301 |

OTHER PUBLICATIONS

Baruch, Martin, Pulse Decomposition Analysis of the digital aterial pulse during hemorrhage simulation, 2011, 5:1, Nonlinear biomedical physics, pp. 1-15.*

Chung, Jin Wook, Reference Values for the Augmentation Index and Pulse Pressure in Apparently Healthy Korean Subjects, 2010, Korean Society of Cardiology, pp. 165-171.*

20120023888, A1, Sep. 20, 2012, U.S. Appl. No. 13/231,703.

Zafiria M. Metafratzi, et al, The Clinical Significance of Aortic Compliance and Its Assessment with Magnetic Resonance Imaging, Journal of Cardiovascular Magnetic Resonance, vol. 4, No. 4, pp. 481-491, 2002.

Nurnberger et al, Dept of Nephrology, University of Essen, Essen, Germany, Diastolic blood pressure is an important determinant of augmentation index and pulse wave velocity in young, healthy males. J Hum Hypertens Mar. 17, 2003 (3):153-8.

Kuecherer et al, Evaluation of aortic compliance in humans, , American Journal of Physiology—Heart and Circulatory Physiology; May 2000 vol. 278 No. 5, H1411-H1413.

Fantin et al, Is augmentation index a good measure of ascular stiffness in the elderly, Oxford Jounals Medicine, Age and Ageing, Nov. 2006; vol. 36, Issue 1, pp. 43-48.

* cited by examiner

NON INVASIVE MONITORING OF ARTERIAL STIFFNESS

FIELD OF THE INVENTION

The invention relates to the noninvasive monitoring of the stiffening of arteries.

BACKGROUND OF THE INVENTION

Arterial stiffness is an important physiological parameter because its increase has been associated with a raised risk of cardiovascular disease and stroke. The underlying mechanisms for both conditions, despite the fact that they both increase arterial stiffness, are however different. One is arteriosclerosis, which is the hardening of the arteries as an age-related effect that has a dilatational and weakening effect on the arterial wall, particularly in the aorta and the cerebral arteries. The other is atherosclerosis, which is characterized by the formation of plaques consisting of lipid accumulation, connective tissue fibers and calcium deposits in certain arterial locations and can affect any artery, but frequently attacks the carotid, cerebral, and the iliac arteries as well as certain locations of the abdominal aorta.

The principal components of the arterial walls are elastin and collagen, both of which constitute about 50% of the dry weight, and smooth muscle and non-fibrous matrix. As is the case in most living tissue, about 70% of wet weight is contributed by water. Both elastin and collagen are fibrous materials but the elastic modulus of collagen is significantly larger than that of elastin. The distribution of elastin and collagen is significantly different for the central, and particularly the thoracic aorta, versus the distal aorta and the peripheral arteries. While in the former elastin is the dominant component, representing about 60% of the fibrous material, in the extrathoracic arteries the relative proportion is reversed, with collagen contributing 70%. The enhanced elastic properties of the thoracic artery allow it to act as a Windkessel pressure storage volume during diastole, maintaining pressure in the arterial system when the heart is closed. The less elastic properties of the abdominal aorta and the peripheral arteries cause the propagation velocity of the arterial pressure pulse to increase as it heads into the periphery.

Certain progressive pathological states will change the elastic property, the stiffness, of the arterial tree. Arteriosclerosis, which affects the central and not the peripheral arteries, is generally understood to be the result of the age-related fracture of elastin fibers, the elastic load-bearing elements of the arterial wall. This deterioration causes the wall to weaken and to stretch, with the result that stress is transferred to the collagenous load bearing elements of the arterial wall much earlier in the rising pressure profile of the passing pressure pulse as compared to the case when the elastic elements are intact. The resultant mean increase in stiffness increases the propagation velocity of the arterial pressure pulse, which in turn accelerates the arrival times of the arterial pulse reflections, with deleterious effects. As an example, it is generally accepted that the timing of the iliac reflection is such that it arrives outside the closed heart, i.e. during diastole, so as to generate the static pressure required to force blood into the coronary arteries, which, at right angles to the ascending aorta, require an aortic no-flow high-pressure condition for optimum perfusion. If the reflected pulse arrives earlier, such as while the aortic valve is still open, the heart has to pump against a high pressure peak, an increased stress that can lead to heart disease. The loss in elasticity, particularly of the thoracic aorta, taxes the heart also by reducing or removing the pressure storage capability of that artery during diastole, forcing the heart to work harder. Specifically, complete loss of the pressure storage capability doubles the workload of the heart. This is one of the reasons for the commonly observed increase in pulse pressure with age.

Another pathology that negatively affects arterial stiffness is atherosclerosis, where the arterial elasticity is reduced due to plaque deposits on the artery's interior. Here the particular dangers are ischemia in the tissue downstream of an obstruction that limits or terminates blood flow, localized weakening of the arterial wall with the possibility of aneurysms, and stroke due to deposits being dislocated and traveling to the lung, the brain, or other sites, with potentially catastrophic consequences.

Early detection of an increase in the arterial stiffness and treatment, particularly through lifestyle changes, could consequently help to prevent the serious consequential complications discussed above. A mile marker against which the effectiveness of treatments and progress toward lowering arterial stiffness can be assessed would be beneficial to both clinicians and patients, making screening as well as long-term follow-up more meaningful and more likely to induce adherence to the required lifestyle changes.

SUMMARY OF THE INVENTION

A computer-implemented method for quantifying arterial stiffness and assigning an AS factor uses executable program on a processor of a computing device. The arterial pulse of an individual is monitored using a monitoring member, such as a finger cuff or other device, having communication means for transmitting and receiving data. The data received from the monitoring member is transmitted to the computing device. Alternatively, the monitoring member can contain the executable program and processor, transmitting data during or at the completion of calculations. The data received by the computing device is processed by the processor, performing a pulse wave analysis. The primary systolic pulse and iliac reflection pulse are extracted from the pulse wave analysis and the time delay between the primary systolic pulse and the iliac reflection pulse determined. The time delay is used by the computing device to calculate a second derivative based least in part, on the time delay. The frequency above zero components are separated from the second derivative and the area of the second derivative determined between a first primary systolic pulse and a first iliac reflection pulse. This area is multiplied by −1 to obtain a positive number and divided by an onset peak amplitude in the second derivative, producing a degree of arterial stiffness. A percentage score is calculated based on the degree of arterial stiffness and input into a historical population database comparing the percentage score with the population data. An AS factor, which is reflective to the degree of featuredness in the arterial pulse and equal to the integration area under the curve of the second derivative, is assigned. Once compared to the population database, the AS factor is compared to an age range.

An electronic meter device is configured to assign a measurement of arterial stiffness by executing a program upon receipt of arterial pulse data by calculating a second derivative to the arterial pulse data, determining an area of said second derivative between a first primary systolic pulse and a first iliac reflection pulse; multiplying said area by −1 to obtain a positive number and dividing said positive number by an onset peak amplitude in said second derivative. The program calculates the second derivative by performing a pulse decomposition analysis and extracting a primary systolic pulse and iliac reflection pulse from the pulse decomposition analysis. The time delay between said primary systolic pulse and said iliac reflection pulse is determined and, using the time delay, a second derivative obtained. The arterial stiffness is measured and compared to arterial stiffness data within a database to assign a percentage to said measurement.

BRIEF DESCRIPTION OF THE DRAWINGS

FIG. 7AC is a graph of time evolutions of the arterial stiffness parameter for the pulse line of FIGS. 3 and 6;

FIG. 9 is a graph displaying the slope factor of the P2P1 PDA parameter as a function of the arterial stiffness factor AS;

DESCRIPTION OF THE INVENTION

Definitions

Figure 1:
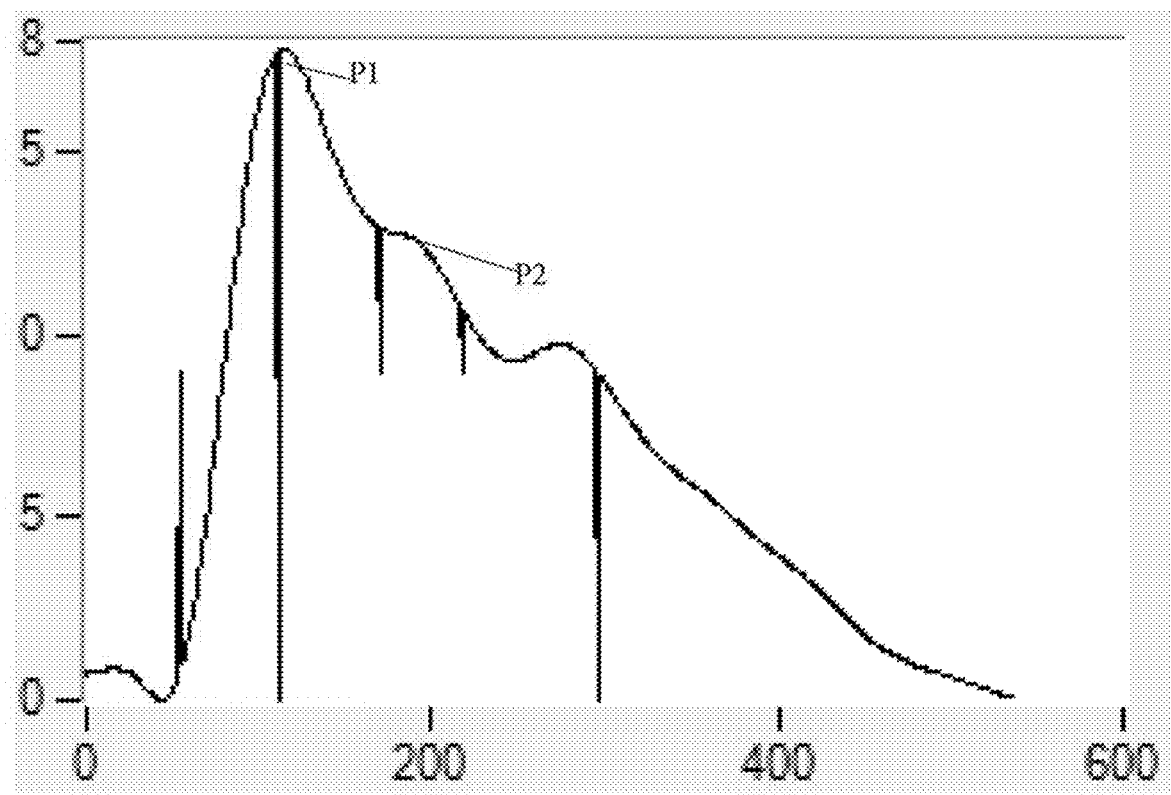
FIG. 1 is a graph of the arterial pulse of a young athlete showing the P1 and P2 locations.

As used herein the term "augmentation index" refers to a ratio calculated from the blood pressure waveform and is a measure of wave reflection and arterial stiffness. Augmentation index is commonly accepted as a measure of the enhancement (augmentation) of central aortic pressure by a reflected pulse wave.

As used herein the term "AS factor" refers to the designation assigned to the degree of arterial stiffness in a subject and is equal to the integration of the area under the curve of the second derivative of the arterial pulse shape between the first negative-going zero crossing and the location of the P3, multiplied by −1.

As used herein the term "CareTaker" refers to the hardware platform, the model, and the algorithm implementation have been described in detail in U.S. Pat. Nos. 8,100,835, 7,087,025, and application Ser. No. 13/231,703 for the determination of Pulse Decomposition Analysis (PDA).

As used herein the term "inzisura" refers to a downward notch in the curve recording aortic blood pressure that occurs between systole and diastole and is caused by backflow of blood for a short time before the aortic valve closes As used herein the terms "features" and "featured" refers to the presence of distinct inversions of curvature on the backend of the arterial pressure pulse profile, clearly displaying, for example, the second systolic pulse and either a deep inzisura past the second systolic pulse or at least a clearly visible and sudden curvature transition, as opposed to a "featureless" pulse profile where none of these features are visually discernible in the pulse profile but can only be extracted through the examination the differentiation(s) of the pulse profile.

As used herein the term "P1" refers to the primary systolic pulse.

As used herein the term "P2" refers to the renal reflection pulse.

P3 is the third component pulse of the Pulse Decomposition Analysis (PDA) formalism. It is the reflection of arterial pressure pulse that originates at the bifurcation of the iliac arteries.

As used herein the term "P2P1" refers to the decrease in arterial wall deflection in response to given systolic pressure indicating arterial stiffness. P2P1 is inversely related to the arterial stiffness, meaning that, for a given systolic blood pressure, P2P1 will decrease if the arterial stiffness increases, and the reverse. P2P1 ratio is calculated using the amplitudes of the renal reflection pulse (P2) and primary systolic pulse (P1).

As used herein the term "T13" refers to the time difference between the arrival of the primary systolic (P1) pulse and the iliac reflection (P3) pulse.

As used herein the term T01 refers to the rise time of the P1 pulse, or the front end of the composite pulse, and is proportional to both the systolic blood pressure and to the arterial stiffness.

As used herein the term "vasoconstriction" refers to the contraction of the smooth muscle of an artery, thereby decreasing the internal diameter of the vessel in a process.

As used herein the term "vasodilation" refers to the relaxation of the smooth muscle of an artery, thereby increasing the internal diameter.

The present invention builds on the approach of tracking blood pressure that is based on the pulse analysis of the peripheral arterial pressure pulse. The approach, referred to as the Pulse Decomposition Analysis (PDA) model, goes beyond traditional pulse analysis by invoking a physical model that comprehensively links the components of the peripheral pressure pulse envelope with two reflection sites in the central arteries. The first reflection site is the juncture between thoracic and abdominal aorta, which is marked by a significant decrease in diameter and a change in elasticity. The second site arises from the juncture between abdominal aorta and the common iliac arteries.

The present invention is a parameter that provides non-invasive measurement and monitoring of how stiff the arteries are, based on calculations deriving data from the presence or absence of features within the pulse.

The disclosed preferably uses the finger cuff, although other blood pressure recording methods can be used, and PDA technology as disclosed in the aforenoted patents and pending application. The finger cuff contains sensors to monitor the arterial pressure pulsations that are then transmitted to the receiving device for analysis. The receiving device can be any computing device capable of analyzing and displaying the received data. Alternatively the data can be analyzed within the finger cuff and only the display transmitted, either wirelessly or through hardwire. The determination of the AS factor is a modular addition to the PDA analysis and is a heretofore unknown derivative that is completely dependent on the results of the PDA analysis, particularly the location of P3.

Pulse analysis, based on the pulse decomposition analysis (PDA) algorithm, of data obtained during lengthy surgical interventions that involved the application of vasoconstrictors and vasodilators provided new insights into the response of previously identified PDA parameters, specifically P2P1 and T13 that are further described below, with respect to changes in arterial stiffness. The data has further helped identify a new parameter, called AS, that tracks arterial stiffness, inclusion of which in PDA facilitates the original algorithm's ability to track intra-patient blood pressure changes by providing the new ability to track arterial stiffness changes, which also provides the new capability to make inter-patient comparisons of arterial stiffness.

The PDA model integrates and goes beyond the findings of a number of studies that have confirmed the existence of the two reflection sites, P2 and P3. A consequence of these reflection sites are two reflected arterial pressure pulses, referred to as component pulses. These pulses counter-propagate to the direction of the single arterial pressure pulse, due to left ventricular contraction, that gave rise to them. In the arterial periphery, and specifically at the radial or digital arteries, these reflected pulses, the renal reflection pulse (P2, also known as the second systolic pulse) and the iliac reflection pulse (P3), arrive with distinct time delays. In the case of P2 the delay is typically between 70 and 140 milliseconds, in the case of P3 between 180 to 450 milliseconds.

Quantification of physiological parameters is accomplished by extracting pertinent component pulse parameters. In the case of the beat-by-beat tracking of blood pressure the PDA model's predictions and previous studies have shown that two pulse parameters are of particular importance. The ratio of the amplitude of the renal reflection pulse (P2) to that of the primary systolic pulse (P1) tracks changes in beat-by-beat systolic pressure. The time difference between the arrival of the primary systolic (P1) pulse and the iliac reflection (P3) pulse, referred to as T13, tracks changes in arterial pulse pressure.

The disclosed is a newly calculated parameter set of the originally disclosed PDA formalism that enables a measure of arterial stiffness, the AS parameter. It is based on distinguishing the arterial pressure pulses associated with stiff arteries from those associated with flexible arteries. Pressure pulses recorded from subjects with flexible arteries, such as young athletes, are featured, while the pressure pulses from subjects with stiff arteries, such as older patients with diagnosed cases of a history of hypertension, which is associated with increased arterial stiffness, are less featured, or not at all.

The analysis of the data collected during well-defined applications of vasoconstrictors and vasodilators has made it possible to establish how in particular P2P1 responds to increases and decreases in arterial stiffness, as well as how the blood pressure/arterial stiffness response of other sections of the pulse can be quantified and utilized.

In particular it has been found that P2P1 is inversely related to the arterial stiffness, meaning that, for a given systolic blood pressure, P2P1 will decrease if the arterial stiffness increases, and the reverse. Physically this is plausible because a compliant artery, meaning with low stiffness, will permit the thoracic aortic diameter to readily distend for a given systolic blood pressure, while a not compliant artery, with high arterial stiffness, will not. Algebraically this can be expressed as follows $$P2P1 \sim \frac{k_1 P_{systole}}{AS}, \quad (1)$$

where $P_{systole}$ is the systolic blood pressure, AS is the arterial stiffness, and $k_1$ is a constant. It is important to note that equation 1 represents an approximate functional relationship, as signified by the proportional sign.

In addition to determining that P2P1 is inversely related to arterial stiffness, another new pulse parameter that has been shown to supplement the existing set of PDA parameters. This is the parameter T01, which refers to the rise time of the P1 pulse, or the front end of the composite pulse. T01 has been found to be proportional to both the systolic blood pressure and to the arterial stiffness.

For a given pulse pressure, the rising pressure pulse will encounter increasing resistance as it stresses the arterial wall, determining the pulse's rise time. If systole rises, while arterial stiffness remains the same, the pulse will stress the arterial wall further, encountering increased resistance from the arterial wall because the increased amplitude of the pulse engages the arterial wall at a deeper wall depth. This increased resistance will delay the rise time of the arterial wall distension due to the rising pressure pulse. Conversely, if systole drops, the arterial wall will offer less resistance, at the same arterial stiffness, because the pulse, not distending the arterial wall as much as with higher systole, stresses it less.

Since with increasing arterial stiffness the same systolic pressure gives rise to a lower arterial wall deflection, which the P2P1 parameter relates to, the slope factor for the conversion from P2P1 to systole will increase, i.e. the same deflection converts to higher systolic blood pressure.

Regarding T13, the slope factor would also be expected to be dependent on the arterial stiffness since the dependence of the velocity of the arterial pressure pulse propagating along the arterial wall in this regard is well known.

If arterial stiffness is increased, for a given blood pressure, the scenario is the same. The rising blood pressure, though it did not change in amplitude, will encounter increased arterial resistance earlier in its rise time than previously; delaying the pressure pulse's fully distending the artery. This motivates the following algebraic expression $$T01 \sim k_2 P_{systole} * AS, \quad (2)$$

where $P_{systole}$ is the systolic blood pressure, AS is the arterial stiffness, and $k_2$ is a constant. These relations make it possible to isolate AS as a function of PDA parameters. Specifically, one obtains $$AS^2 \sim \frac{T01}{P2P1} \quad (3)$$

It would therefore appear that it is possible to determine the arterial stiffness through readily measured PDA parameters alone. While this is the case for intra-patient data, it is not useful as a parameter to compare and assess the relative arterial stiffness of different subjects/patients. The reason is the fact that P2P1 actually is subject to two different effects that are related to blood pressure and arterial stiffness. As previously discussed, increases in systole distend the thoracic aorta relative to the abdominal aorta, giving rise to the direct dependence of systole/P1P2. But there is another effect, due to age—and/or disease—related increases in arterial stiffness, that affects P2P1. Known in the medical terminology as the "augmentation index", it is well known that the P2 component pulse returns earlier in stiffer arteries and, when the overall pressure pulse envelope is observed in the arterial periphery, partly merges with the primary pulse, adding an amplitude "shoulder" to the P1 pulse.

As an example, FIG. 1 displays the arterial pulse of a young athlete. The P2 pulse, at 200, is clearly visible and lags well behind the primary pulse P1 at about 100.

Figure 2:
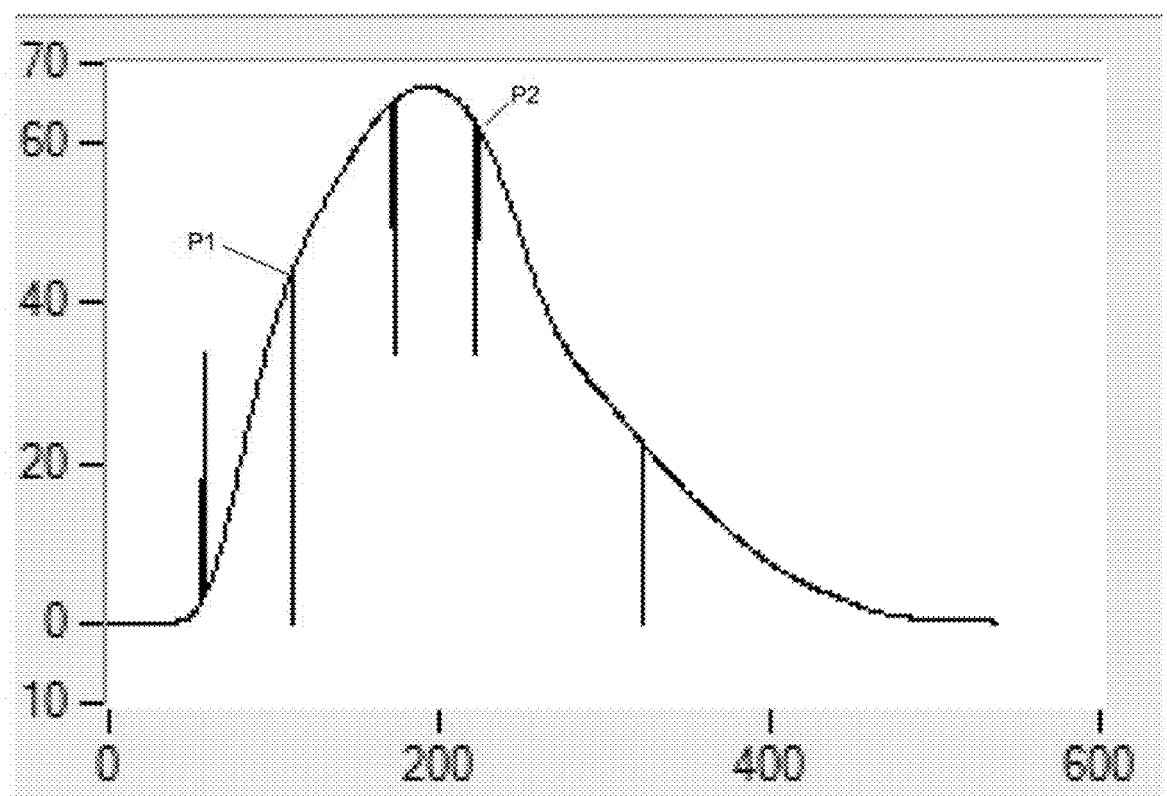
FIG. 2 is a graph of the arterial pulse of a 55 year old catheter lab patient showing the P1 and P2 locations.

In a 55 year old catheter lab patient of FIG. 2 the two pulses have merged because the P2 pulse follows the P1 so closely as to cause them to overlap. P1 is indicated by the vertical line at 130 while P2 is indicated by the two short vertical lines bracketing 200. P2, following closely behind P1 has merged with P1 as an additive shoulder. For this individual, P1 and P2 are clearly resolved.

Figure 3:
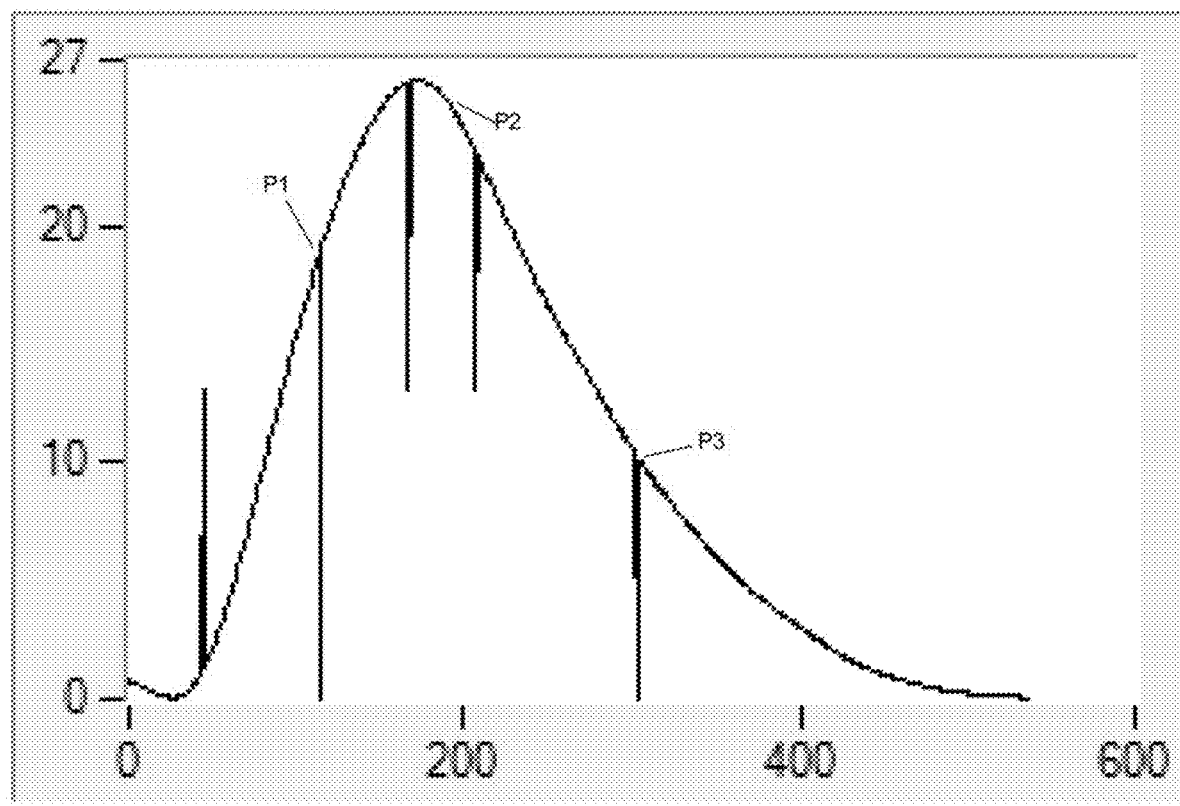
FIG. 3 is a graph of the arterial pulse of a Pancreaticoduodenectomy surgery patient showing the P1 and P2 locations.

In FIG. 3 the arterial pulse of a pancreaticoduodenectomy surgery patient is illustrated wherein P1 and P2 have essentially merged. Even the inzisura in front of P3, indicated by the vertical line at 310, is essentially indistinguishable.

It is therefore illustrated that P2P1 is subject to two different effects that, for comparison purposes, tend to cancel each other. While a large amplitude response to blood pressure changes by the P2P1 ratio is a good indication, suggesting that the thoracic aorta is flexible, a large baseline amplitude, unless accompanied by a high pressure, is not a good indication because it suggests that the central arteries are "fast" because they are stiff. Without external information, such as the age or independently obtained blood pressure readings, the two effects cannot be separated for a given patient, making it impossible to obtain an "absolute" arterial stiffness assessment. It is for this reason that the "augmentation index" has had only moderate success and is generally used only to assess older patients.

As an alternative, T01 alone could be considered as a measure of arterial stiffness. However, while it is not subject to an age-related "offset" in the way P2P1 is, its strong dependence on blood pressure variations make it unsuitable to use T01 as a sole indicator of arterial stiffness.

Based on the foregoing, one factor that distinguishes the arterial pressure pulses associated with stiff arteries from those associated with flexible arteries is, respectively, the absence of features versus the presence of features. The pressure pulses from flexible arteries are featured, while the pressure pulses from stiff arteries are less featured, or not at all. FIGS. 1-3 make this point clearer.

What distinguishes the displayed pulse shapes is the increasing lack of features. In the case of the young athlete (FIG. 1), with highly flexible arteries, the component pulses are clearly visible. In the case of the 55 year old catheter lab patient (FIG. 2) this is clearly less the case. Finally, in the case of a patient requiring an extremely long and invasive surgical procedure, the component pulses are no longer readily distinguishable in the pulse envelope (FIG. 3).

The presence or relative absence of these component pulse features relate to arterial stiffness is based on the same as the T01 response: the higher the arterial stiffness, the longer the rise time of any blood pressure variation. However it applies here to the distensive effects on the arterial wall due to each component pulse, which a stiffer arterial wall will resist and delay. Consequently the responses due the different component pulses will meld together, smoothed over by the wall's mechanical filtering effect.

Figures 7A, 7B, 7C:
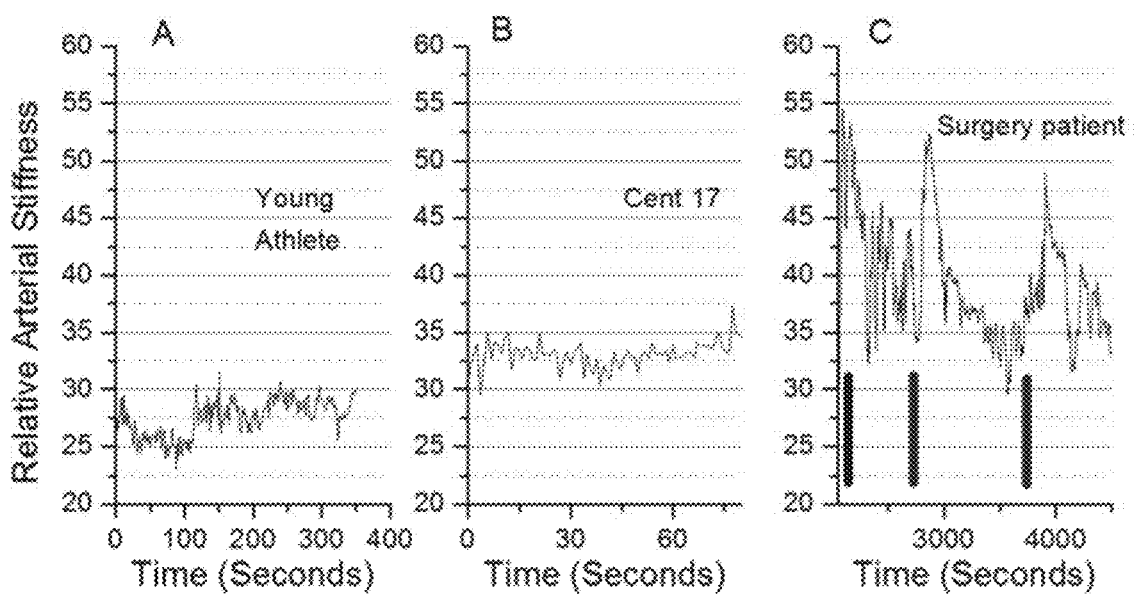
FIG. 7A is a graph of time evolutions of the arterial stiffness parameter for the pulse line of FIGS. 1 and 4.
FIG. 7B is a graph of time evolutions of the arterial stiffness parameter for the pulse line of FIGS. 2 and 5.

The PDA arterial stiffness factor (AS) takes this "featuredness" into account quantitatively through an integration of the second derivative of the pulse shape. It is also normalized against amplitude and heart rate. FIGS. 7A-7C present time evolution examples for the heart beat pulses presented in FIGS. 1-3.

Figure 9:
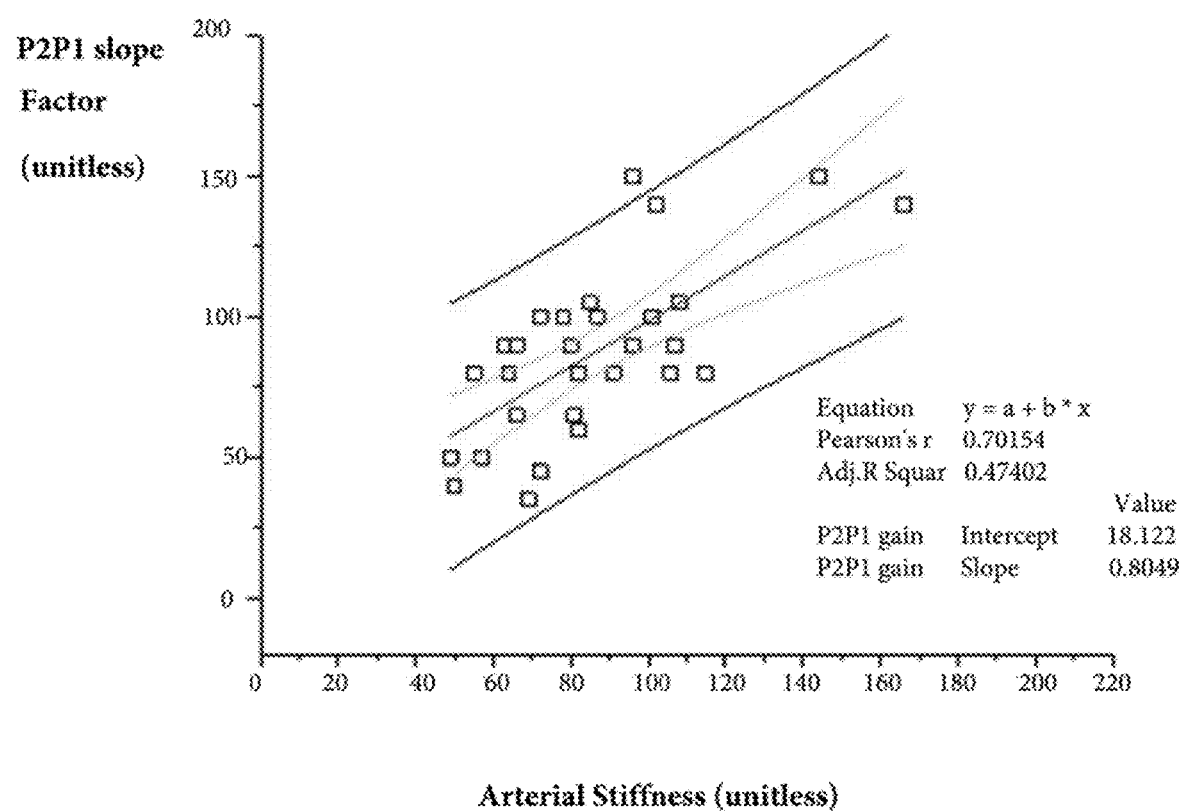

Since the P2P1 parameter is a measure of the thoracic aorta's distensibility as a function of systolic blood pressure, it would be expected to be dependent on arterial compliance or its inverse, arterial stiffness. FIG. 9 displays the P2P1 slope factor, obtained from best fit chi^optimizations of P2P1 versus catheter systolic pressure, as a function of the AS parameter for each patient from the previously mentioned study of abdominal surgery patients as well as the patients discussed in detail here. Also displayed in FIG. 9 is the straight line of a linear fit that is the basis for the equation, also displayed in FIG. 9, used to calculate the P2P1 slope factor using a given AS factor.

The integral for determining the AS factor is:

$$S = -1 \int_{ZC}^{t_{p3}} \frac{d^2 \text{Pulse}}{dx^2}$$

Where AS=arterial stiffness factor, ZC=first negative-going zero crossing, $t_{p3}$=time location of the P3 component pulse, $d^2\text{Pulse}/dx^2$=second derivative of the arterial pressure signal.

The disclosed effect is even blood-pressure independent because, as results have shown, pressure pulses retain their "features" in elevated blood pressure conditions if the arteries are flexible. The issue is then how to quantify the fact that a pressure pulse is featured, less so, or not. It is well known that derivatives extract and enhance "features" relative to large and slowly-varying background signals. As an example, derivative spectroscopy is a well-established technique used in spectroscopy to enhance and isolate very weak absorption lines. The situation here is similar, characterized by a large overall pulse shape with features of modest comparative amplitude. It is known that the overall frequency content of the pulse shape is low, extending in bandwidth no more that 25-30 Hz because of the arterial mechanical filtering effect. The aim of the differentiation is then to separate the "higher" frequency components, those above zero, from the low-frequency, those below zero, overall pulse shape.

Figure 4:
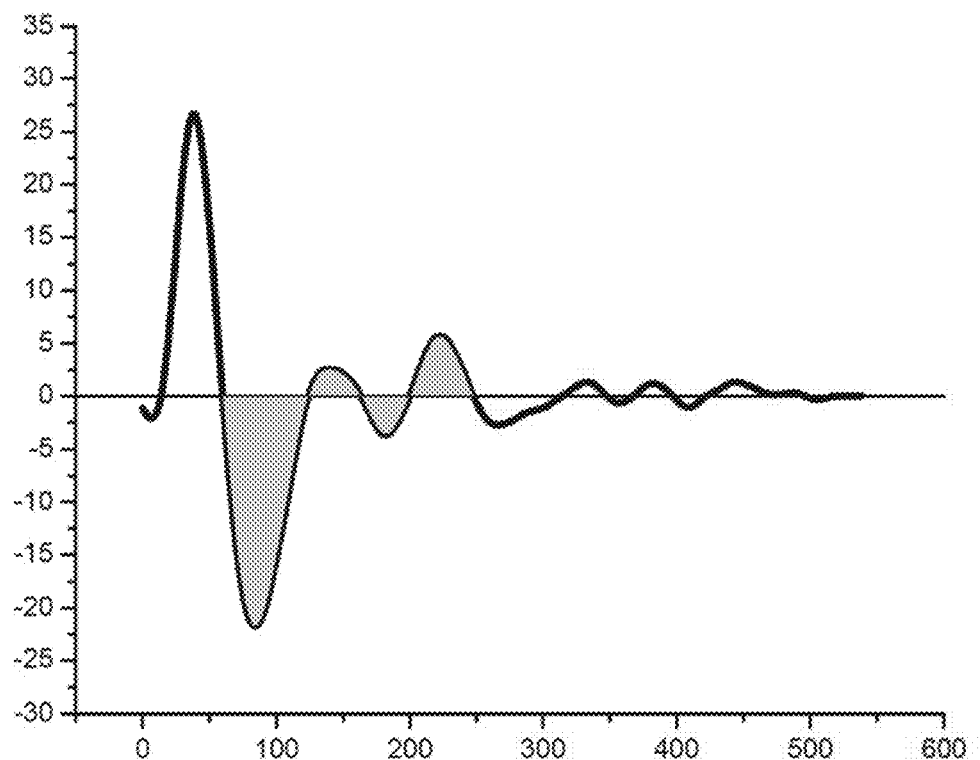
FIG. 4 is a graph illustrating the second derivatives of the arterial pulse of FIG. 1.
Figure 5:
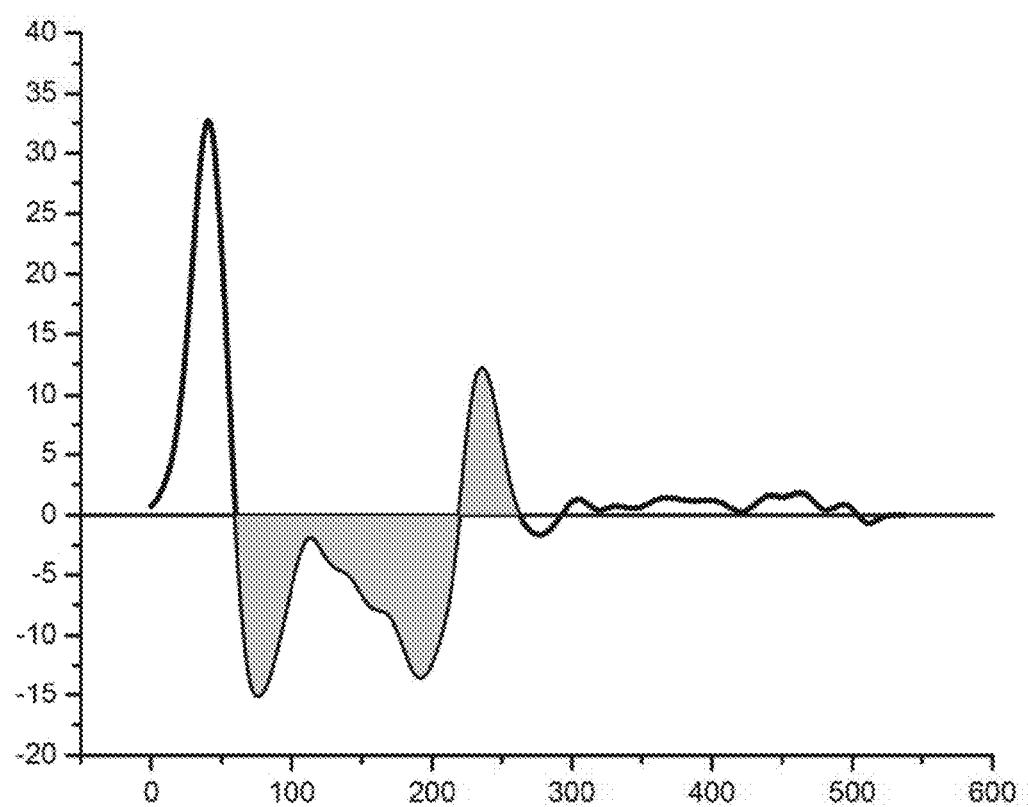
FIG. 5 is a graph illustrating the second derivatives of the arterial pulse of FIG. 2.
Figure 6:
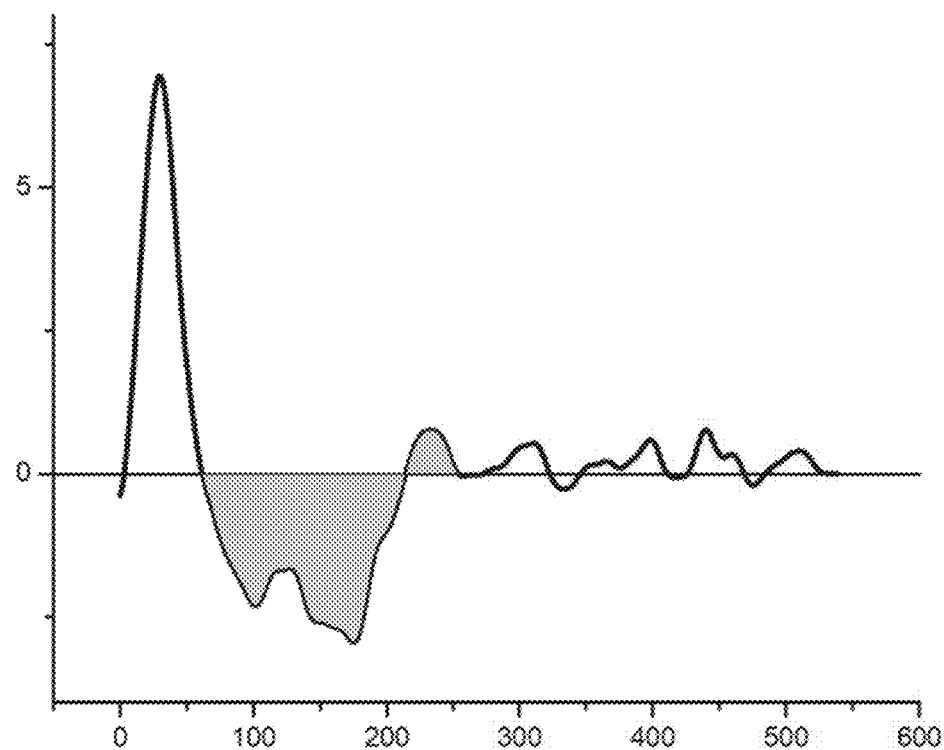
FIG. 6 is a graph illustrating the second derivatives of the arterial pulse of FIG. 3.

FIG. 4-6 display the second derivatives of the pulse shapes displayed in

FIGS. 1-3 respectively. The second derivative was chosen because it is symmetric with the original pulse shapes, facilitating identification of the respective pulse features. Of note also is that the second derivative is inverted relative to the original pulse. The second derivative line shapes amplify the effect that was already visible in the pulse shapes. There are fewer zero-crossings and fewer pronounced inversions when comparing FIGS. 4-6. Although simply counting inversions would appear to provide necessary data, due to the small number of crossing, the quality of the data would be low. Furthermore, it is clear from inspection of FIG. 5, data point 105, that there can be "almost" crossings, i.e. parts of the curve that come within a small interval of zero but do not cross it, that would go undetected. An example of an "almost" crossing is shown in FIG. 5 at data point 105, where the curve approaches zero but does not cross it. At this data point the trace of the second derivative returns almost to zero but does not cross it. A better approach is to integrate the area between the curve and zero, as illustrated in FIGS. 4-6, from the zeroth crossing and the position of P3. In each of the figures this area has been shaded for clarification. The integration is sign-dependent, in other words the area above the curve will subtract from the larger negative area below the curve. To make the integration value comparable between different data runs and patients, it is normalized by dividing it by the amplitude of the first positive peak, which corresponds to the onset inversion of P1. It is also multiplied by −1, yielding a positive value.

Physiologically the results of these comparative integrations are obvious: an arterial wall characterized by low stiffness will be able to readily follow the features that are due to the component pressure pulses of the traversing arterial pressure pulse envelope. As a result, the line shapes displayed in FIG. 4, producing an AS factor of 26.9, are narrow and of high amplitude as compared to the first inversion peak. In fact they are powerful enough to cross zero. In FIG. 5, with an AS factor of 35.3, this is clearly less the case as the increased stiffness of the arterial wall reduces its ability to respond, increasing the area under the curve. Finally, the effect of the large arterial stiffness is evident in FIG. 6, with an AS factor of 55.3. This curve has further reduced inversions, further increasing the area under the curve.

FIG. 7, which displays time-evolutions of the arterial stiffness parameter for the pulse signals presented in FIGS. 1-3 and 4-6, puts the results in perspective. FIGS. 7A (young athlete) and 7B (central line patient) display the relative difference in arterial stiffness, which is plausible given their different ages and health conditions. FIG. 7C displays the dynamics of the stiffness parameter for the surgery patient as a result of the application of a vasodilator 702 and two subsequent applications of vasoconstrictors 704 and 706 to attempt to compensate for the "overshoot" of the vasodilator 702. The observed response of the proposed arterial stiffness parameter matches the proposed physiological model well. In response to the vasodilator 702 the AS parameter decreases significantly and rebounds with each application of the vasoconstrictors 704 and 706.

Figure 11:
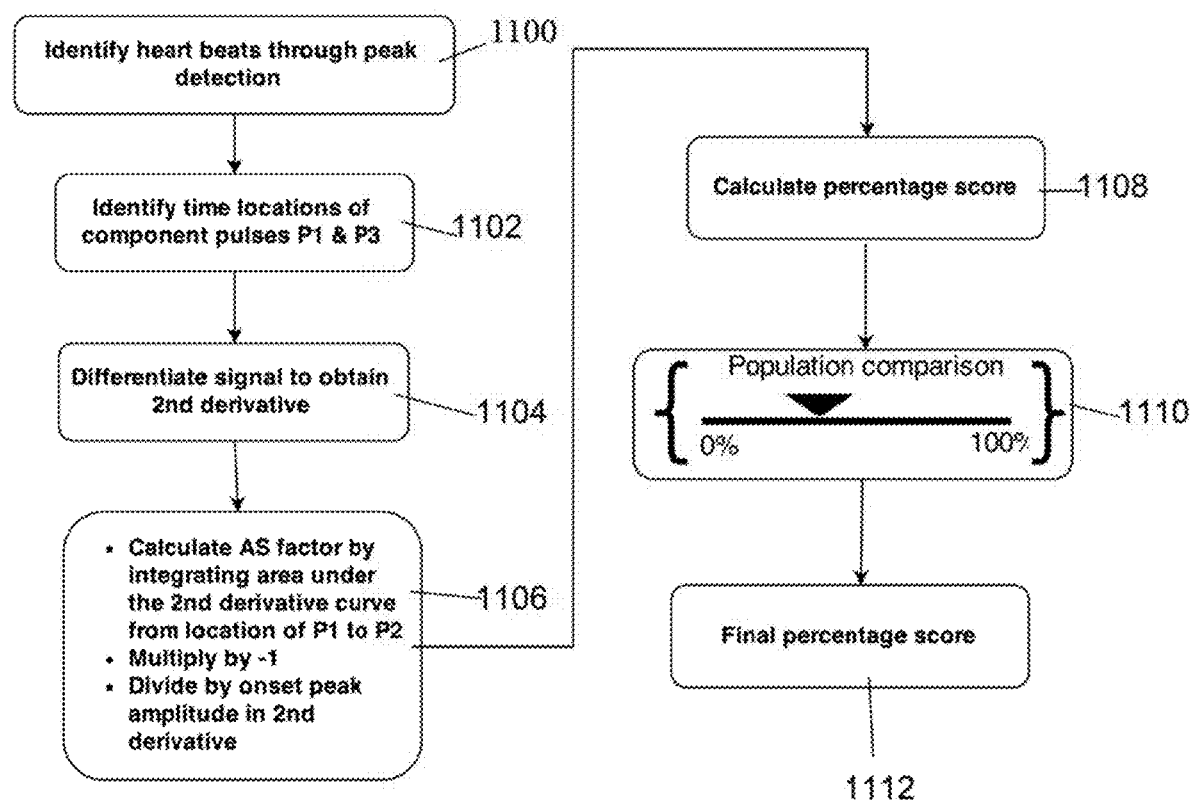
FIG. 11 is a flow chart of the computer process for determining and arterial stiffness.

To determine the AS factor, the data, as set forth above is processed in accordance with the flow chart of FIG. 11. The initial step is for the computing device to identify heart beats through peak detection 1100 from which the time location, or time delay, of the component pulses P1 and P3 signals are identified 1102. The result identifies the presence or absence of features within the pulse. The computing device takes the resulting signal and differentiates the signal to obtain the $2^{nd}$ derivative 1104 to start the calculations on the AS factor. The calculations integrate the area under the $2^{nd}$ derivative curve from the location of P1 to P2. This area is then multiplied by −1 and divided by the onset peak amplitude in the $2^{d}$ derivative 1106. From this calculation the percentage score is calculated 1108 which is then compared to a bar chart showing zero to 100 percent arterial stiffness population scores 1110 to produce a final percentage score, or AS factor 1112

The percentage score is generated by comparing a given score to the maximum/minimum range in a database. The relevance of age comes later. If a subject is 70 and has medium stiff arteries (50% score), that is readily acceptable and easily within the norm. However, a young person and with medium stiff arteries, would be above the norm.

In order to investigate the correspondence between arterial stiffness and the PDA AS factor quantitatively, the response of the AS factor in response to the administration of vasoconstrictors and vasodilators in surgery patients was examined. Specifically, 35 patients scheduled for major abdominal surgery were consented to participate in this IRB approved study if arterial monitoring was required for hemodynamic monitoring and patient comorbidities. Each patient was monitored with a radial arterial catheter and a CareTaker using a finger cuff applied to the contralateral thumb. Hemodynamic variables were measured from both devices for the first thirty minutes of the surgical procedure including the induction of anesthesia.

After a stable signal was recorded all patients were induced under general anesthesia by using propofol (2-4 mg/kg) and fentanyl 250 ug. Tracheal intubation was facilitated by the administration of rocuronium (0.6 mg/kg). Mechanical ventilation was started using a volume controlled ventilator to maintain an adequate saturation and an end-carbon dioxide of 35 mmHg. Inhalational anesthetic (Isoflurane) was added to maintain a BIS of less the 45. Vasoactive drugs were used to maintain a MAP greater than 60 mmHg.

In the case of the arterial catheter data the criteria for exclusion were as follows: A. visual inspection of the data was used to identify sections of obvious catheter failure, characterized by either continuous or spurious nonsensical reading. B. sections contaminated by excessive motion artifact were identified as such if the peak detection algorithm was no longer able to identify heart beats, as evidenced by inspection of the resulting implausible and discontinuous inter-beat interval spectrum.

Figure 8:
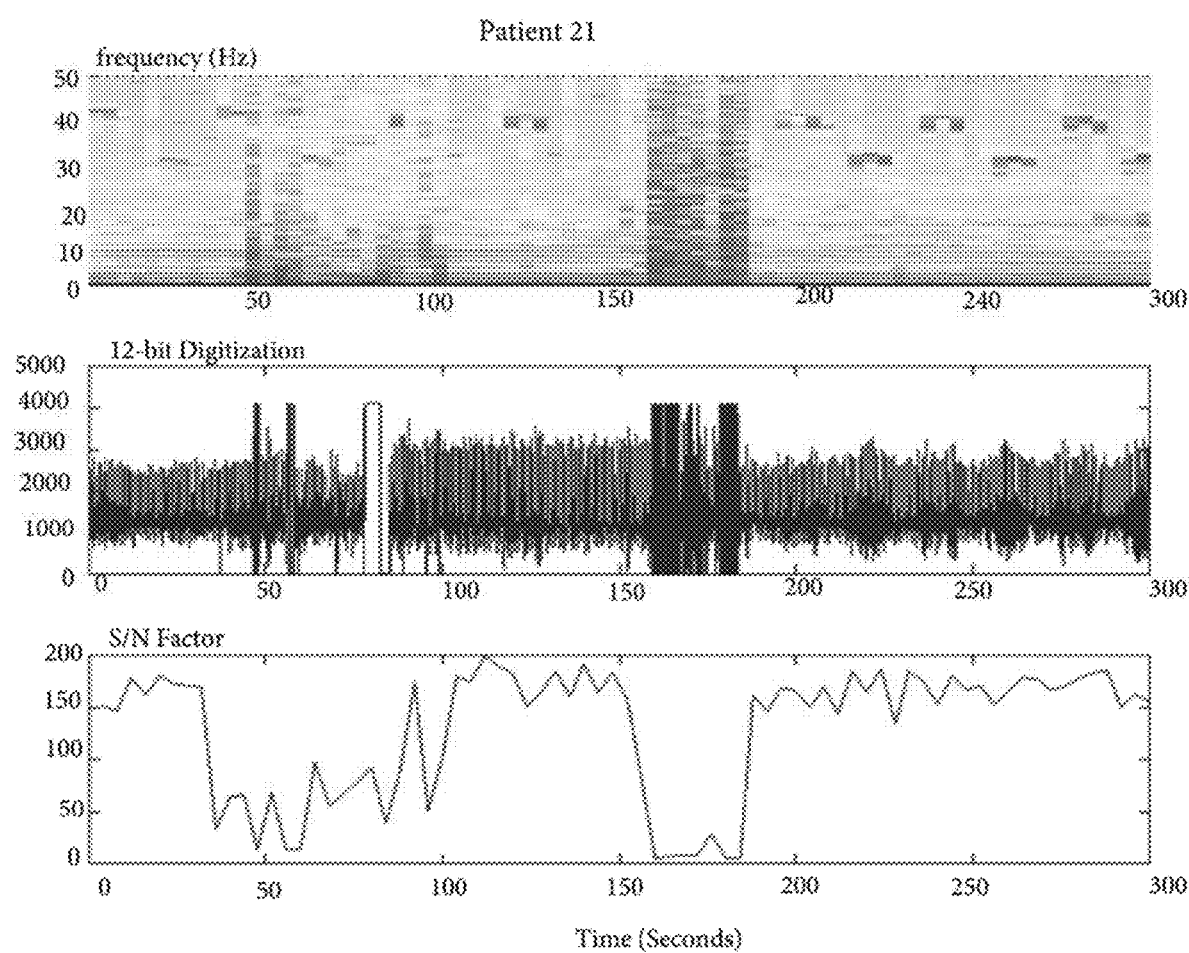
FIG. 8 is a graph indicating the effect of noise sources on the frequency spectrum of the CareTaker signal.

In the case of the CareTaker data a signal/noise factor based on the ratio of the variances of the physiological signal band to the noise band, a standard approach, was obtained using Fourier spectral analysis over an 8-second with 1 second overlap, was used to identify poor quality data sections. The frequency range of the band associated with the physiological signal was set to 1-10 Hz, while the noise band was set to the 100-250 Hz frequency range, which is subject to ambient noise but contains no signal relevant to the base band phenomena of the arterial pressure pulse or its propagation characteristics. Data sections characterized by low noise feature low high-frequency spectral amplitudes and high low-frequency spectral amplitudes as well as "structured" physiological bands, i.e. significant amplitude variations between the harmonic bands, motivating the calculation of the ratio of the frequency-based variances of the relevant bands. Data sections with an SNR below 80 were excluded from the analysis. An example of the results of such a noise analysis is presented in FIG. 8.

Two types of analyses were performed; one investigated the specificity/sensitivity of the AS factor in response to the application of a vasoconstrictor, while the other sought to correlate the pre-surgery AS factor with the likelihood of the patient requiring vasopressor intervention subsequently during the surgical procedure.

As part of the specificity/sensitivity analysis the time locations of administration of vasoactive drugs were obtained from the medical record and the corresponding time locations in the CareTaker data stream were identified. The mean of the AS factor values within a five minute time window before administration was determined, as well as the AS factor of the first plateau after administration. In cases where no plateau was reached, the value at the point of reversion was taken. A receiver-operator-curve (ROC) analysis was then used to determine specificity/sensitivity. ROC analyses, which involve plotting the true positive rate against the false positive rate, are an effective approach to assessing the classification capability of diagnostic tests, i.e. vasopressor applied yes/no, where the generally accepted AUC for an effective test is larger than 0.7, with perfect discrimination corresponding to AUC=1.0, while a test with no discriminatory capability will have an area in the vicinity of 0.5.

Figure 10:
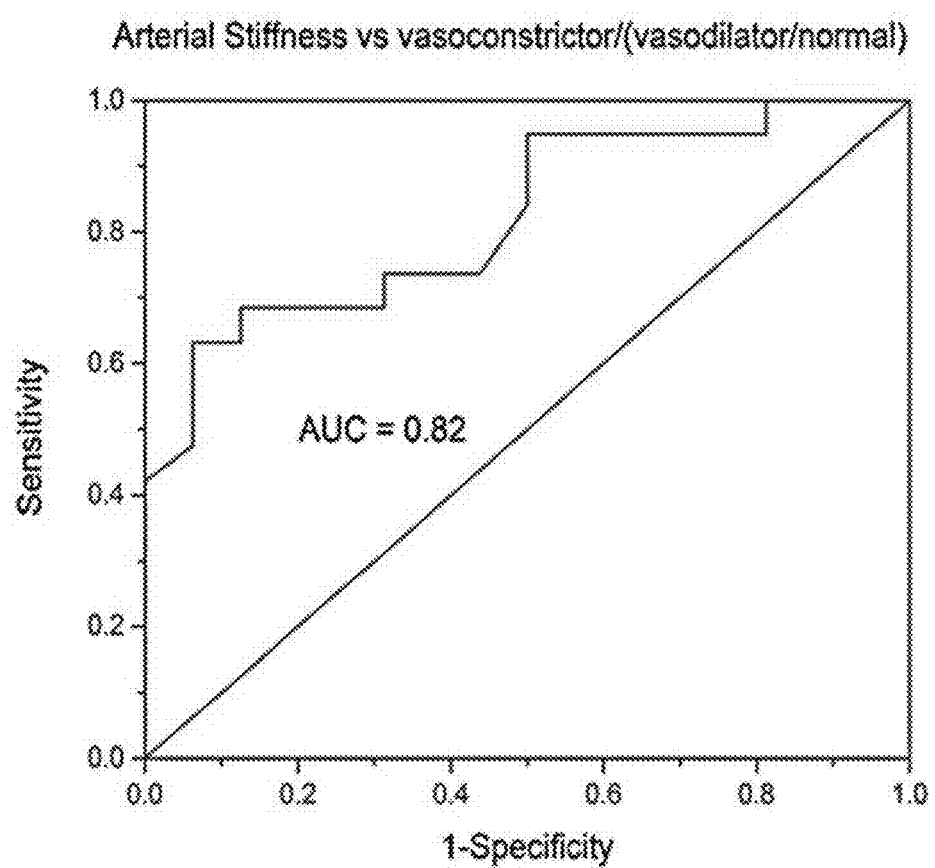
FIG. 10 is a receiver operator curve (ROC) of the AS factor in response to a vasoconstrictor (state 1) or a vasodilator/no vasopressor (state 2)

The two states used for the ROC analysis were the application of a vasoconstrictor (state 1) as opposed to the application of a vasodilator or no application of a vasopressor (state 2). FIG. 10 presents the results of the ROC analysis, with an area-under-curve of 0.82, suggesting that the AS factor is tracks arterial stiffness changes well.

With regard to correlating the pre-surgery AS factor with the likelihood of the patient requiring vasopressor intervention subsequently during the surgical procedure pre-surgery CareTaker data was available only for 6 of the 35 patients. The results are as follows:
 a. four patients had an AS of 28 (considered low) or less: of these
 b. two patients had two constrictor applications each when their blood pressure dropped precipitously.
 c. two patients had a numerous constrictor applications to maintain blood pressure: 4 & 6, respectively
 d. One patient had an AS of 52 (considered high) and received 6 vasodilator applications to prevent blood pressure from spiking.
 e. One patient had an AS of 36 (normal range) and received a single vasoconstrictor application This data would suggest that patients with an AS of 28 or less have a very high chance of requiring a vasoconstrictor, while those with an initially very high AS will require a vasodilator. The results of the study support the physical model that has been presented to as a hypothesis of the relationship between the AS factor and arterial stiffness.

The hardware platform, the model, and the algorithm implementation have been described in detail in U.S. Pat. No. 8,100,835, 7,087,025, and application Ser. No. 13/231,703 which are incorporated herein as though recited in full.

Broad Scope of the Invention

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims (e.g., including that to be later added) are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language of the present invention or inventions should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example."

While in the foregoing we have disclosed embodiments of the invention in considerable detail, it will understood by those skilled in the art that many of these details may be varied without departing from the spirit and scope of the invention.

What is claimed is:

1. In a non-invasive arterial stiffness monitoring system, a computer-implemented method for quantitatively measuring relative arterial stiffness of a patient based on component pulse features comprising the steps of:
 a. monitoring said patient's arterial pulse through use of a single location sensor to detect said patient's arterial pressure pulse, said arterial pressure pulse having component pulses comprising a primary systolic pulse, a renal reflection pulse, and an iliac reflection pulse;
 b. gathering the detected arterial pressure pulse as data from said sensor with a processor of a computing device and storing said data on a non-transitory readable medium in said processor;
 c. running a pulse decomposition analysis with said processor as the data is received from said sensor, said pulse decomposition analysis identifying component pulse features of said arterial pressure pulse component pulses, said component pulse features being a primary systolic pulse location peak, a renal reflection pulse location peak, and an iliac reflection pulse location peak within each of said component pulses;
 d. determining, with said processor, an arterial stiffness (AS) factor for said patient based on said pulse decomposition analysis, said AS factor being independent of blood pressure variations, comprising the steps of:
  i. calculating a time window between said primary systolic pulse location peak and said iliac reflection pulse location peak;
  ii. calculating a second derivative curve of said arterial pressure pulse within said time window;
  iii. determining an integral of said second derivative curve between said primary systolic pulse and said iliac reflection pulse;
  iv. multiplying said integral by −1 to obtain a positive number; and
  v. dividing said positive number by an onset peak amplitude in said second derivative curve;
 e. determining, with said processor, an AS factor score for said patient by generating an AS percentage by comparing said AS factor for said patient to a range of historical AS percentages stored in a database within said processor, and comparing said AS percentage to population data stored within said processor;
 f. assigning said AS factor score to said patient, wherein said AS factor score corresponds to a quantitatively measurable degree of relative arterial stiffness of said patient; and
 g. monitoring stiffening of the arteries of said patient based on said AS factor score.

2. The method of claim 1 wherein said sensor is within a finger cuff.

3. The method of claim 1 wherein said processor determines said AS factor score by comparing said AS factor for said patient to a bar chart of zero to 100 percent reflecting AS factors for said historical AS percentages previously entered and stored in said processor.

4. The method of claim 1 wherein said AS factor is equal to an integration area under said second derivative curve from a first negative crossing of said first primary systolic pulse location to said first iliac reflection pulse location.

5. The method of claim 1 wherein in the step of calculating said AS factor said processor executes the formula of:

$$AS = -1 \int_{ZC}^{t_{p3}} \frac{d^2 \text{Pulse}}{dx^2}$$

wherein AS=arterial stiffness factor, ZC=a first negative-going zero crossing, $t_{p3}$=a time location of the iliac reflection pulse, and $d^2\text{Pulse}/dx^2$=a second derivative of the arterial pressure signal.

6. The method of claim 1 wherein said AS factor and AS factor score provide for the tracking of intra-patient arterial stiffness changes independent of blood pressure changes and provide for inter-patient comparisons of arterial stiffness.

7. The method of claim 1 wherein monitoring of said AS factor prior to surgery indicates the likelihood of said patient requiring vasopressor or vasodilator intervention.

8. The method of claim 1, wherein identifying said component pulse features comprises identifying a presence or relative absence of said component pulse features; wherein, said area of said second derivative curve corresponds to said presence or relative absence of said features; and wherein, a lower AS factor reflects a greater presence of features thus indicating flexible arteries and a higher AS factor reflects a greater absence of features thus indicating a measurable degree of arterial stiffness.

9. The method of claim 1, further comprising repeated monitoring of said AS factor score of said patient over time to track changes in said AS factor score, wherein said changes in AS factor score indicate changes in arterial stiffness of said patient.

10. A non-invasive, computer-implemented system for quantifying arterial stiffness to monitor stiffening of arteries of an individual comprising:
   a. monitoring said individual's arterial pressure pulse using a single location sensor capable of reading arterial pressure pulse data;
   b. running a pulse decomposition analysis of said arterial pressure pulse data as received by said processor to analyze component pulses, said component pulses comprising a primary systolic pulse, a renal reflection pulse, and an iliac reflection pulse;
   c. extracting from said component pulses, a primary systolic pulse location peak, a renal reflection pulse location peak, and an iliac reflection pulse location peak;
   d. determining a time window between said primary systolic pulse location peak and said iliac reflection pulse location peak;
   e. calculating a second derivative curve of an arterial pressure pulse based on said time window;
   f. determining an integral of said second derivative;
   g. multiplying said integral by −1 to obtain a positive number;
   h. dividing said positive number by an onset peak amplitude in said second derivative to obtain an arterial stiffness (AS) factor, said AS factor corresponding to an arterial stiffness percentage generated by comparing said AS factor for said individual to a range of historical AS percentages stored in a database within said processor; and
   i. assigning an Arterial Stiffness (AS) factor score for said individual by determining, with said processor, an AS factor score for said patient by comparing said arterial stiffness percentage for said individual with historical arterial stiffness percentages of collected population data stored within said processor;
   wherein said AS factor score is independent from blood pressure variations and reflective of a presence or relative absence of component pulse features, and wherein a relative absence of features indicates arterial stiffness.

11. The method of claim 10, wherein said AS factor is equal to an integration area under said second derivative curve from a first negative going crossing of said first primary systolic pulse location to said first iliac reflection pulse location.

12. The method of claim 10 wherein in calculating said AS factor said computer executes the formula of:

$$AS = -1 \int_{ZC}^{t_{p3}} \frac{d^2 \text{Pulse}}{dx^2}$$

wherein AS=arterial stiffness factor, ZC=a first negative-going zero crossing, $t_{p3}$=a time location of the iliac reflection pulse, and $d^2\text{Pulse}/dx^2$=a second derivative of the arterial pressure signal.

13. The method of claim 10 wherein said sensor is within a finger cuff.

14. In an arterial stiffness monitoring system, an electronic meter device for quantitatively measuring relative arterial stiffness of an individual based on component pulse featuredness to identify and monitor stiffening of arteries in said individual comprising:
   a. a finger cuff sensor configured to monitor arterial pressure pulse of an individual, said arterial pressure pulse having component pulses comprising a primary systolic pulse, a renal reflection pulse, and an iliac reflection pulse; and
   b. a computing device configured to receive said arterial pressure pulse as data from said sensor, said computing device comprising:
      a processor;
      a non-transitory readable medium in said processor; and
      a display mechanism;
   wherein, said processor reads said arterial pressure pulse data received from said sensor and runs a pulse decomposition analysis to identify component pulse features of said arterial pressure pulse components, said component pulse features comprising a primary systolic pulse peak, a renal reflection pulse peak, and an iliac reflection pulse peak; and
   wherein said processor calculates an integral of a second derivative curve based on a time window between said primary systolic peak and said iliac reflection pulse peak, multiplies said integral by −1 to obtain a positive number and divides said positive number by an onset peak amplitude in said second derivative curve to determine a degree of featuredness, and calculates an AS factor based on said featuredness as represented by $$S = -1 \int_{ZC}^{r_{p3}} \frac{d^2 \text{Pulse}}{dx^2}$$

wherein said processor calculates an AS factor score, said AS factor score is a quantitative measurement of arterial stiffness of said individual, and said AS factor score is independent of blood pressure variations in said individual.

15. The device of claim 14 wherein said AS factor score is determined for said individual by generating an AS percentage corresponding to said AS factor by comparing said AS factor for said individual to a range of historical AS percentages stored in a database within said processor as a bar chart of zero to 100 percent, and comparing said AS percentage to population data stored within said processor.

16. The device of claim 14 wherein monitoring of said AS factor score over time tracks arterial stiffness and is a mile marker against applied treatments.

* * * * *